United States Patent [19]

Kleemann et al.

[11] Patent Number: 4,851,557
[45] Date of Patent: Jul. 25, 1989

[54] COPPER-CONTAINING POLYMERS, A PROCESS FOR THEIR PREPARATION AND THEIR USE AS FUNGICIDES

[75] Inventors: Stephan G. Kleemann, Schriesheim; Guenter Claus, Edingen, both of Fed. Rep. of Germany

[73] Assignee: Benckiser-Knapsack GmbH, Ladenburg, Fed. Rep. of Germany

[21] Appl. No.: 875,738

[22] Filed: Jun. 18, 1986

[30] Foreign Application Priority Data

Jun. 20, 1985 [DE] Fed. Rep. of Germany ....... 3522000

[51] Int. Cl.$^4$ .............................................. C07F 1/08
[52] U.S. Cl. ................................... 556/110; 514/499; 514/500; 71/67; 71/97
[58] Field of Search ................ 556/110; 514/499, 500; 71/67, 97

[56] References Cited

U.S. PATENT DOCUMENTS

| | | | |
|---|---|---|---|
| 2,924,551 | 2/1960 | Harwood et al. | 556/110 X |
| 2,939,759 | 6/1960 | Scalera et al. | 556/110 X |
| 3,200,106 | 8/1965 | Dickson et al. | 556/110 X |
| 3,351,658 | 11/1967 | Bersworth | 556/110 X |
| 3,507,892 | 4/1970 | Bersworth | 556/110 X |
| 3,686,244 | 8/1972 | Marks | 556/110 X |
| 3,927,206 | 12/1975 | Blank et al. | 556/110 X |
| 4,048,324 | 9/1977 | Kohn | 556/110 X |
| 4,098,602 | 7/1978 | Seymour et al. | 556/110 X |
| 4,181,786 | 1/1980 | Mune et al. | 556/110 X |
| 4,268,455 | 5/1981 | Langer, Jr. et al. | 556/110 X |
| 4,319,019 | 3/1982 | Lehmann et al. | 556/110 X |
| 4,393,179 | 7/1983 | Hoppe et al. | 556/110 X |
| 4,409,358 | 10/1983 | Kraft et al. | 556/110 X |
| 4,497,737 | 2/1985 | Sargeson et al. | 556/110 X |

FOREIGN PATENT DOCUMENTS

| | | | |
|---|---|---|---|
| 349269 | 3/1979 | Austria | 556/110 x |
| 3432569 | 2/1986 | Fed. Rep. of Germany | 556/110 X |

*Primary Examiner*—Paul F. Shaver
*Attorney, Agent, or Firm*—Foley & Lardner, Schwartz, Jeffery, Schwaab, Mack, Blumenthal & Evans

[57] ABSTRACT

Copper-amine complexes comprised of a water-soluble copper salt and a polyamide-amine can be used as fungicides without the addition of ammonia, and they form firmly adhering coatings on leaf surfaces.

18 Claims, No Drawings

4,851,557

COPPER-CONTAINING POLYMERS, A PROCESS FOR THEIR PREPARATION AND THEIR USE AS FUNGICIDES

BACKGROUND OF THE INVENTION

The present invention relates to copper-containing amine polymers, to a process for their preparation, and to their use as fungicides.

The use of copper salts in agriculture for the control of fungal diseases in crop plants is a practice of long-standing. To ensure the effectiveness of a copper treatment over a prolonged period, inorganic copper salts like copper oxychloride have been used which are sparingly soluble or insoluble in water. Oily formulations of copper salts based on low-molecular organic carboxylic acids have also been disclosed; these formulations have an activity comparable to the inorganic copper salts but a considerably lower copper content, and are less suitable for the treatment of plants because of their oily basis.

The art has therefore developed fungicidal agents in which copper salts of organic acids, which are themselves only sparingly soluble in water, are brought into aqueous solution by complex-formation with ammonia, as described in West German Offenlegungsschriften No. 2,807,293 and No. 2,202,448, in U.S. Pat. No. 3,900,504, and in British patent specifications No. 599,443 and No. 593,416. When these aqueous solutions are applied to the surfaces to be treated, particularly to crop plants, the ammonia evaporates along with the solvent; as a result, the sparingly soluble copper salts are reformed on the treated surface, effecting a slow release of copper ions and, hence, a persistent fungicidal action.

But these salts display only a poor adhesion to the plant surfaces, in the extent that they are washed off in solid form (although not dissolved) by rain. Accordingly, the literature cited above limits the suitability of these substances as fungicides mainly to the treatment of textiles and wood, with no mention of their suitability for plant protection.

Copper salts displaying better adhesion are obtained, in accordance wtih British patent specification No. 1,394,990 and European patent application No. 0 039 788, by converting copper salts of polycarboxylic acids (acrylic acid or methacrylic acid polymers) into water-soluble, complex compounds by treatment with ammonia, and then applying them in complexed form. Once again, evaporation of the ammonia results in the reformation, on the leaf surface, of the sparingly soluble copper salt, from which copper ions having a fungicidal action are slowly released. It is a disadvantage of these solutions that a considerable excess of ammonia has to be added to achieve adequate complexing of the copper ions; consequently, the solutions effect a strongly alkaline reaction and damage the plants when applied. Moreover, a considerable odor nuisance arises through the evaporation of the ammonia.

Synthetic resins containing copper bound as a complex can be prepared from Mannich bases, free from epoxide groups, and have been used as pigments, curing catalysts, antifoaming agents and adhesion promoters (see West German Offenlegungsschrift No. 3,045,251). But no information has been available regarding their use as fungicides.

SUMMARY OF THE INVENTION

It is therefore an object of the present invention to provide copper preparations which can be employed as fungicides, especially in agriculture, and which require the addition of little or no ammonia, but which nevertheless produce coatings that adhere firmly to leaf surfaces.

It is also an object of the present invention to provide a method for treating plants, using the copper preparations mentioned above, to combat fungal infections.

It is yet another object of the present invention to provide a process for preparing a fungicidal composition based on copper-amine complexes of polyamide-amines.

It has now been found, surprisingly, that copper-amine complexes of polyamide-amines, if appropriate with the addition of up to 25% of ammonia relative to the amount of polyamide-amine, are capable to a high degree of forming stable, aqueous solutions of copper complexes and that copper complex solutions of this type exhibit good fungicidal properties compared with inorganic copper salts and copper polyacrylate or preparations of copper carboxylates. In contrast with the previously known preparations, the copper ion is not only present in the aqueous solution, but is also present, after application to the surface to be protected, in the form of the polymer-amine complex, from which the copper is slowly and uniformly released to the plant.

In accomplishing the foregoing objects, there has thus been provided, in accordance with one aspect of the presently claimed invention, a copper-amine complex containing a water-soluble copper salt and an amount of a polyamide-amine which is at least sufficient for complex-formation. In one preferred embodiment, the copper-amine complex of the present invention comprises an aqueous solution wherein the complex is present in a concentration of about 0.01 to 10% by weight.

There has also been provided, in accordance with another aspect of the present invention, the use of the above-described copper-amine complex as a fungicide, for example, in plants.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

For purposes of this description, the term "polyamide-amines" is used to denote polymers containing free and/or substituted amide groups and, in addition, free and/or substituted amine groups. In accordance with this definition, the class polyamideamines suitable for use in accordance with the present invention contains the following representative moieties:

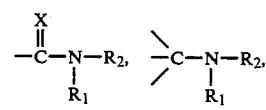

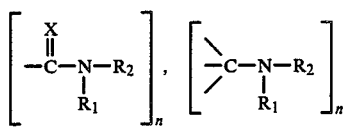

wherein $R_1$ and $R_2$ are hydrogen atoms or linear, cyclic or branched, saturated or unsaturated alkyl, aryl or aralkyl groups, either substituted or unsubstituted; and X is oxygen or sulfur.

The copper-amine complexes according to the present invention can be prepared by adding a readily soluble copper salt, such as copper(II) acetate, copper(II) sulfate or other customary copper compound, in solid or solution form, to an aqueous solution of a polyamide-amine. The copper-amine complexes can also be prepared by reacting copper salts of weak or readily volatile acids with the polyamide-amines in aqueous solution. In this reaction, the concentration of the reactants is selected to be within an approximately molar ratio. A greater excess of the copper(II) salt is disadvantageous; an excess of polyamide-amine or ammonia (if any is added) causes no problems, but the use of less than an equivalent results in precipitation, particularly upon dilution with water to concentrations suitable for application.

Preparation is usually carried out at temperatures of 20°–100° C., preferably at an elevated temperature and especially at temperatures of 30°–60° C.

The polyamide-amines to be used in preparing the copper-amine complexes of the present invention are known compounds which can be obtained by the customary processes of bulk, solution, precipitation, emulsion or suspension polymerization, and also by selective degradation reactions, as described, for example, in our own West German patent application P 34 32 569.7, which is hereby incorporated by reference.

When the plant protection agent according to the present invention, diluted to useful concentrations, is applied to articles, plants or parts of plants to be treated, a copper-polymer film is formed when the solution dries. The film thus formed is sparingly soluble or insoluble in water, adheres firmly to the treated surface of the article or plant, and retains its fungicidal action over a prolonged period of time.

The new complexes possess an excellent long-term fungicidal action which exceeds that of known copper-containing fungicides. They can, therefore, be employed in all cases where undesirable growth or attack by microorganisms takes place.

The active polyamide-amine compounds and the biocidal agents prepared with them, in accordance with the present invention, are distinguished over known compositions by being very well tolerated by plants. The new plant protection agents also have the advantage that they can be applied from a purely aqueous solution. Their use therefore results in less environmental pollution than is associated with treatments employing known copper compounds.

It is not necessary to use the copper-containing polymers in the pure form as plant protection agents. For example, the biocidal agents of the present invention can also contain customary additives, such as wetting agents, stabilizers and antioxidants, and, if appropriate, other active compounds as well, such as herbicides, insecticides, growth regulators or even other fungicides. Applications involving these additional agents can therefore be effected in a single operation.

Solutions prepared according to the present invention preferably contain copper in an amount of 0.01–10%, with concentrations of 0.01–0.5% usually being adequate for use as plant protection agents. Solutions of a higher concentration are, therefore, normally diluted with water or aqueous solutions of other active compounds prior to application.

In the following illustrative examples of the present invention, a filter-paper substrate was coated with different polymeric copper-amine complexes of the present invention (see Examples 1–11 below). Copper content was then determined, before and after copious treatment of the substrate with water, to measure the retention behavior of each polymer with respect to the complexed copper. To make this determination, 0.2 to 0.4 g of each copper-polymer solution was dried on filter paper. The filter paper was then placed in 100 ml of distilled water (250-fold to 500-fold excess), and the amount of copper which dissolved in the course of 3 hours was determined by titration.

The filtration determinations were carried out using three different approaches:

(a) The filter paper was removed from the solution with tweezers, the paper and the tweezers were rinsed, and the total liquid was then buffered with 5 g of sodium acetate and titrated with 0.05M $Na_2EDTA$ solution.

(b) The filter paper was removed from the solution with tweezers, the paper and tweezers were rinsed and the total liquid rendered strongly acid with dilute (1:1) hydrochloric acid; 5 g of sodium acetate were added to the liquid and the pH of the liquid was adjusted to 5.7 with concentrated ammonia, after which titration was carried out as described under (a).

(c) The determination was carried out as described under (b), but the solution was decanted off, the filter paper was removed, and the beaker was rinsed out. The results of the titrations by these three methods are shown in Table I. For the sake of clarity, the reported data relate directly to the percentage content of copper retained by each polymer under the above-described conditions.

The K-values reported in the following examples were determined at 30° C. by the method of H. Fikentscher, *Cellulosechemie* 13: 48–64 and 71–74 (1932). (K here denotes k×1,000.). The determination of the K-value of the acrylonitrile copolymer was carried out in dimethylformamide. The K-value for the product of the catalyzed reaction between ethylenediamine and triethylene glycol was determined in sodium nitrate solution, after the polymer had been precipitated in an excess of acetone and dried in vacuo at 50° C. The concentration was 0.5 g of precipitated polymer in 100 ml of 1N sodium nitrate solution. All the reported quantities in the examples relate to weight.

EXAMPLE 1

0.32 g of sulfur in 33.1 g of ethylenediamine were initially placed in a 500 ml, three-necked flask equipped with a KPG stirrer and a reflux condenser, and were mixed, with stirring, with 33.1 g of triethylene glycol. 26.5 g of polyacrylonitrile fibers containing 7% of allyl sulfonate and having a K-value of 82.9 were then added, and the mixture was heated to a bath temperature of 170° C. After 2.7 hours at this temperature, 75 g of water were added to the resulting product, and the temperature was kept at 50° C. for an additional 30 minutes. After the mixture thus prepared was cooled to room temperature and 1.1 g of H$_2$O$_2$ in 4.5 g water added, the mixture was heated at 100° C. for 30 minutes, diluted with additional water to a concentration of 4.6% and then separated from undissolved particles through a 0.1 mm sieve.

The resulting solution contained a polyamide-amine according to West German patent application No. 34 32 569.7, having a K-value of 34.1. 1.57 parts of copper(II) acetate·1 H$_2$O were introduced, in portions at 50° C., into 20 parts of the polyamide-amine solution, and the mixture was stirred at this temperature for 15 minutes. A stable, blue-green solution having a copper content of 2.3% was thereby formed.

EXAMPLE 2

0.32 g of sulfur in 33.1 g of ethylenediamine were initially placed in a 500 ml three-necked flask equipped with a KPG stirrer and a reflux condenser, and were mixed, with stirring, with 63.1 g of triethylene glycol. 26.5 g of polyacrylonitrile fibers containing 7% of allyl sulfonate and having a K-value of 80.5 were then added, and the mixture was heated to a bath temperature of 170° C. After 2.7 hours at this temperature, 75 g, of water were added to the resulting product, and the temperature is kept at 50° C. for an additional 30 minutes. After the mixture was cooled to room temperature and 1.1 g of H$_2$O$_2$ in 4.5 g of water added, the mixture was heated at 100° C. for 30 minutes, diluted with additional water to a concentration of 4.9%, and then separated from undissolved particles through a 0.1 mm sieve.

The resulting solution contained a polyamide-amine according to West German patent application P 34 32 569.7 having a K-value of 33.5. 1.57 parts of copper(II) acetate·1 H$_2$O were introduced, in portions at 50° C., into 20 parts of the polyamide-amine solution, and the mixture was stirred at this temperature for 15 minutes. A stable, blue-green solution having a copper content of 2.3% is formed.

EXAMPLE 3

0.32 g of sulfur in 33.1 g of ethylenediamine were initially placed in a 500 ml three-necked flask equipped with a KPG stirrer and a reflux condenser, and were mixed, with stirring, with 63.1 g of triethylene glycol. 26.5 g of polyacrylonitrile fibers containing 7% of allyl sulfonate and having a K-value of 82.9 were then added, and the mixture was heated to a bath temperature of 175° C. After 3 hours at this temperature, 75 g of water were added to the resulting product, and the temperature was kept at 50° C. for an additional 30 minutes. After the mixture was cooled to room temperature and 1.1 g of H$_2$O$_2$ in 4.5 g of water added, the mixture was heated at 100° C. for 30 minutes, diluted with additional water to a concentration of 5.4%, and then separated from undissolved particles through a 0.1 mm sieve.

The resulting solution contained a polyamide-amine according to West German patent application P 34 32 569.7 having a K-value of 25.8. 1.57 parts of copper(II) acetate·1 H$_2$O were introduced, in portions at 50° C., into 20 parts of the polyamide-amine, and the mixture was stirred at this temperature for 15 minutes. A stable, blue-green solution having a copper content of 2.3% was formed.

EXAMPLE 4

0.32 g of sulfur 33.1 g of ethylenediamine were initially placed in a 500 ml three-necked flask equipped with a KPG stirrer and a reflux condenser, and were mixed, with stirring, with 93.1 g triethylene glycol. 26.5 g of polyacrylonitrile fibers containing 7% of allyl sulfonate and having a K-value of 82.9 were then added, and the mixture was heated to a bath temperature of 170° C. After 3.5 hours at this temperature, 70 g of water are added to the resulting product, and the temperature was kept at 50° C. for an additional 30 minutes. After 1.1 g of H$_2$O$_2$ in 4.5 g of water were added, the mixture was heated at 100° C. for 30 minutes, diluted with additional water to a concentration of 22%, and then separated from undissolved particles through a 0.1 mm sieve.

The resulting solution contained a polyamideamine according to West German patent application P 34 32 569.7 having K-value of 23.0. 3.21 parts of copper(II) acetate·1 H$_2$O$_2$ were introduced, in portions at 50° C. and with the addition of 10 parts of water, into 10 parts of the polyamide-amine solution, and the mixture was stirred at this temperature for 15 minutes. A stable, greenish solution having a copper content of 4.4% was formed.

EXAMPLE 5

3.74 parts of copper(II) acetate·1 H$_2$O were introduced, in portions at 50° C. and with the addition of 7 parts of water, into 13 parts of a solution, in 100 parts of water, containing 22 parts of a polyamide-amine according to West German patent application P 34 32 569.7 prepared in accordance with Example 4, and the mixture was stirred at this temperature for 15 minutes. A stable, dark green solution having a copper content of 5.0% was formed.

EXAMPLE 6

0.6 part of copper(II) acetate·1 H$_2$O were introduced, in portions at 50° C. and with the addition of 5 parts of water, into 5 parts of a solution containing 25 parts of a polyamide-amine (Retaminol EC ® made by Bayer) in 100 parts of water, and the mixture was stirred at this temperature for 15 minutes. A stable, dark blue solution having a copper content of 1.8% was formed.

EXAMPLE 7

0.32 g of sulfur in 33.1 g of ethylenediamine were initially placed in a 500 ml three-necked flask equipped with a KPG stirrer and a reflux condenser, and were mixed, with stirring, with 93.1 g of triethylene glycol. 26.5 g of polyacrylonitrile fibers containing 7% of allyl sulfonate and having a K-value of 82.9 were then added, and the mixture was heated to a bath temperature of 175° C. After 3.5 hours at this temperature, 75 g of water were added to the resulting mixture, and the temperature was kept at 50° C. for an additional 30 minutes. After the mixture was cooled to room temperature and 1.1 g of H$_2$O$_2$ in 4.5 g of water added, the mixture was heated at 100° C. for 30 minutes, diluted with additional water to a concentration of 28%, and then separated from undissolved particles through a 0.1 mm sieve.

The resulting solution contained a polyamide-amine having a K-value of 22.2. 1.57 parts of copper(II) acetate·1 H$_2$O were added, in portions at 50° C. and with the addition of 15 parts of water, to 5 parts of the polyamide-amine solution, and the mixture was stirred at this temperature for 15 minutes. A stable, green solution having a copper content of 2.3% is formed.

EXAMPLE 8

0.64 g of sulfur in 62.1 g of ethylenediamine were initially placed in a 500 ml three-necked flask equipped with a KPG stirrer and a reflux condenser, and were mixed, with stirring, with 62.1 g of triethylene glycol. 53.1 g of polyacrylonitrile fibers containing 7% of allyl sulfonate and having a K-value of 82.9 were then added, and the mixture was heated to a bath temperature of 175° C. After 5.5 hours at this temperature, 60 g of water were added to the resulting product, and the temperature was kept at 90° C. for an additional 30 minutes. After the resulting mixture was cooled to room temperature and 2.3 g of $H_2O_2$ in 4.5 g of water added, the mixture was heated at 100° C. for 30 minutes, diluted with additional water to a concentration of 41%, and then separated from undissolved particles through a 0.1 mm sieve.

The resulting solution contained a polyamide-amine having a K-value of 10.9. 6.19 parts of copper(II) acetate·1 $H_2O$ were introduced, in portions at 50° C. and with the addition of 10.25 parts of water, into 9.75 parts of the polyamide-amine solution, and the mixture was stirred at this temperature for 15 minutes. A stable, dark green solution having a copper content of 7.5 % was formed.

EXAMPLE 9

0.38 g of sulfur in 39.7 g of ethylenediamine were initially placed in a 500 ml three-necked flask equipped with a KPG stirrer and a reflux condenser, and were mixed, with stirring, with 34.5 g of triethylene glycol. 31.9 g of polyacrylonitrile fibers containing 7% of allyl sulfonate and having a K-value of 80.7 were then added, and the mixture was heated to a bath temperature of 175° C. After 3 hours at this temperature, 75 g of water were added to the resulting mixture, and the temperature was kept at 50° C. for an additional 30 minutes. After the mixture was cooled to room temperature and 1.1 g of $H_2O_2$ in 4.5 g of water added, the mixture was heated at 100° C. for 30 minutes, diluted with additional water to a concentration of 20%, and then separated from undissolved particles through a 0.1 mm sieve.

The resulting solution contained in polyamide-amine having a K-value of 22.0. 79 parts of copper(II) acetate·1 $H_2O$ are introduced, in portions at 50° C. and with the addition of 147 parts of water, in 274 parts of the polyamide-amine solution, and the mixture was stirred at this temperature for 15 minutes. A stable, dark green solution having a copper content of 5.0% was formed.

EXAMPLE 10

Comparison Example 1.2 parts of copper(II) acetate·1 $H_2O$ were introduced, in portions at 50° C. and after adjusting the pH to a value of 6.0 by adding 15.3 parts of water and NaOH, into 20 parts of a solution, in 100 parts of water, containing 35 parts of a polyacrylic acid homopolymer having a K-value of 22.3. The resulting mixture was stirred at this temperature for 15 minutes. A stable, dark green solution having a copper content of 1.1% was formed.

EXAMPLE 11

Comparison Example 1.2 parts of copper(II) acetate·1 $H_2O$ were introduced, in portions at 50° C. and after adding 10 parts of water and adjusting the pH to a value of 6.0 by adding 11.3 parts of 25% strength ammonium hydroxide solution, into 20 parts of a solution, in 100 parts of water, containing 35 parts of a polyacrylic acid homopolymer having a K-value of 22.3. The resulting mixture was stirred at 50° C. for 15 minutes. A stable, dark blue solution having a copper content of 0.9% was formed.

TABLE I

| Example | Undissolved copper (in weight percentage) | | |
|---|---|---|---|
| | Method (a) | Method (b) | Method (c) |
| No. 1 | 23.3 | 21.3 | 21.8 |
| No. 2 | 23.9 | 23.0 | 22.0 |
| No. 3 | 22.9 | 21.2 | 18.5 |
| No. 4 | n.d. | 62.4 | 62.7 |
| No. 5 | n.d. | 47.4 | 49.9 |
| No. 6 | n.d. | 77.2 | 77.1 |
| No. 7 | 23.8 | 23.1 | 22.7 |
| No. 8 | n.d. | 26.3 | 30.3 |
| No. 9 | 52.1 | 56.3 | 58.1 |
| No. 10 | 0 | 0 | 0 |
| No. 11 | 0 | 0 | 0 |
| Copper acetate | 0 | 0 | 0 | n.d. = not determined

What is claimed is:

1. A copper-amine complex comprising a water-soluble copper salt and an amount of a polyamide-amine comprised of a carbonic acid amide moiety, said amount being at least sufficient for complex-formation.

2. A copper-amine complex as claimed in claim 1, further comprising ammonia in an amount of up to 25% by weight of said polyamide-amine.

3. A copper-amine complex as claimed in claim 1, wherein the polyamide-amine is present in a 1.5-molar to 5-molar excess, relative to amine groups in relation to copper ions.

4. An aqueous solution comprising a copper-amine complex as claimed in claim 1.

5. A solution as claimed in claim 4, wherein said complex is present in a concentration of about 0.01–10% by weight.

6. A solution as claimed in claim 5, wherein said concentration is about 0.1–7.5% by weight.

7. A solution as claimed in claim 4, further comprising, in a concentration of up to 20% by weight, a dispersion of an acrylic acid or methacrylic acid homopolymer or copolymer.

8. A process for the preparation of copper-amine complexes as claimed in claim 1, which comprises the step (A) of mixing a first aqueous solution of said water-soluble copper salt with a second aqueous solution of said polyamide-amine.

9. A process as claimed in claim 8, further comprising the step of adding aqueous or gaseous ammonia to the result of step (A).

10. A process as claimed in claim 8, wherein said copper salt and said polyamide-amine are reacted at an elevated temperature.

11. A process as claimed in claim 10, wherein said copper salt and said polyamide-amine are reacted at between 30° C. and 60° C.

12. A method of using a copper-containing aqueous solution, comprising the step of applying an aqueous solution that comprises a copper-amine complex as claimed in claim 1 to a surface of a plant.

13. A method as claimed in claim 12, wherein said aqueous solution further comprises at least one from the group consisting of a herbicide, an insecticide, a growth regulator and another fungicide.

14. A method as claimed in claim 12, wherein said copper-amine complex is present in a concentration of about 0.01–10% by weight.

15. A method as claimed in claim 12, wherein said carbonic acid amine moiety is selected from the group consisting of

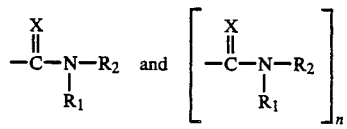

wherein $R_1$ and $R_2$ are (i) hydrogen atoms or (ii) linear, cyclic or branched, saturated or unsaturated alkyl, aryl or aralkyl groups, either substituted or unsubstituted; and X is oxygen or sulfur.

16. A copper-amine complex as claimed in claim 1, wherein said carbonic acid amine moiety is selected from the group consisting of

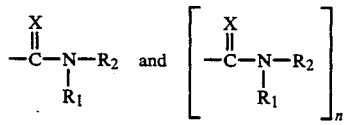

wherein $R_1$ and $R_2$ the same or different, and each is (i) a hydrogen atom or (ii) a linear, cyclic or branched, saturated or unsaturated alkyl, aryl or aralkyl group, either substituted or unsubstituted; and X is oxygen or sulfur.

17. A method as claimed in claim 12, wherein said copper-amine complex comprises a water-soluble copper salt and a polyamide-amine comprised of an amine moiety selected from the group consisting of

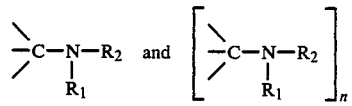

wherein $R_1$ and $R_2$ are the same or different and each is (i) a hydrogen atom or (ii) a linear, cyclic or branched, saturated or unsaturated alkyl, aryl or aralkyl group, either substituted or unsubstituted, and X is oxygen or sulfur.

18. A copper-amine complex as claimed in claim 1, said copper-amine complex comprising a water-soluble copper salt and a polyamide-amine comprised of an amine moiety selected from the group consisting of

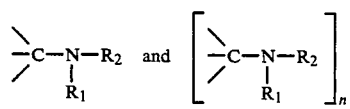

wherein $R_1$ and $R_2$ are the same or difference and each is (i) a hydrogen atom or (ii) a linear, cyclic or branched, saturated or unsaturated alkyl, aryl or aralkyl group, either substituted or unsubstituted, and X is oxygen or sulfur.

* * * * *